(12) United States Patent
Burrows et al.

(10) Patent No.: US 7,252,381 B2
(45) Date of Patent: Aug. 7, 2007

(54) OPHTHAMOSCOPE

(75) Inventors: Clive Harrold Thomas Burrows, Hazlemere (GB); Kelvyn Church, Reading (GB); Stephen Church, Farnborough (GB); David Ernest Lane Freeman, South Croydon (GB); James Robert Arnold Matthews, Bracknell (GB)

(73) Assignee: Keeler Limited, Windsor (GB)

( * ) Notice: Subject to any disclaimer, the term of this patent is extended or adjusted under 35 U.S.C. 154(b) by 282 days.

(21) Appl. No.: 10/540,297

(22) PCT Filed: Aug. 25, 2004

(86) PCT No.: PCT/GB2004/003630

§ 371 (c)(1),
(2), (4) Date: Jun. 21, 2005

(87) PCT Pub. No.: WO2005/020804

PCT Pub. Date: Mar. 10, 2005

(65) Prior Publication Data

US 2006/0077345 A1 Apr. 13, 2006

(30) Foreign Application Priority Data

Aug. 28, 2003 (GB) ................... 0320096.1

(51) Int. Cl.
*A61B 3/14* (2006.01)
(52) U.S. Cl. ............ 351/207; 351/214; 351/218
(58) Field of Classification Search ....... 351/207, 351/214, 218, 205, 200, 246
See application file for complete search history.

(56) References Cited

U.S. PATENT DOCUMENTS 3,586,424 A * 6/1971 Schenk et al. .......... 351/213

* cited by examiner

*Primary Examiner*—Hung Xuan Dang
(74) *Attorney, Agent, or Firm*—Barnes & Thornburg, LLP

(57) ABSTRACT

An ophthalmoscope has illuminating optics (10) for projecting a beam of light into an eye under examination and imaging optics (14) for creating an image of said eye for viewing by a user. The imaging optics comprises an objective lens system (16) and an eye piece lens system (20). Two corneal reflex stops (138 and 148) are positioned one on either side of the corneal image formed by the objective lens system. The stops block reflections from the cornea of the eye under examination over a range of distances of the ophthalmoscope from the eye. The use of the two corneal reflex stops results in the precise positioning of the ophthalmoscope relative to the eye under examination not being critical to the blocking of the corneal reflex.

34 Claims, 8 Drawing Sheets

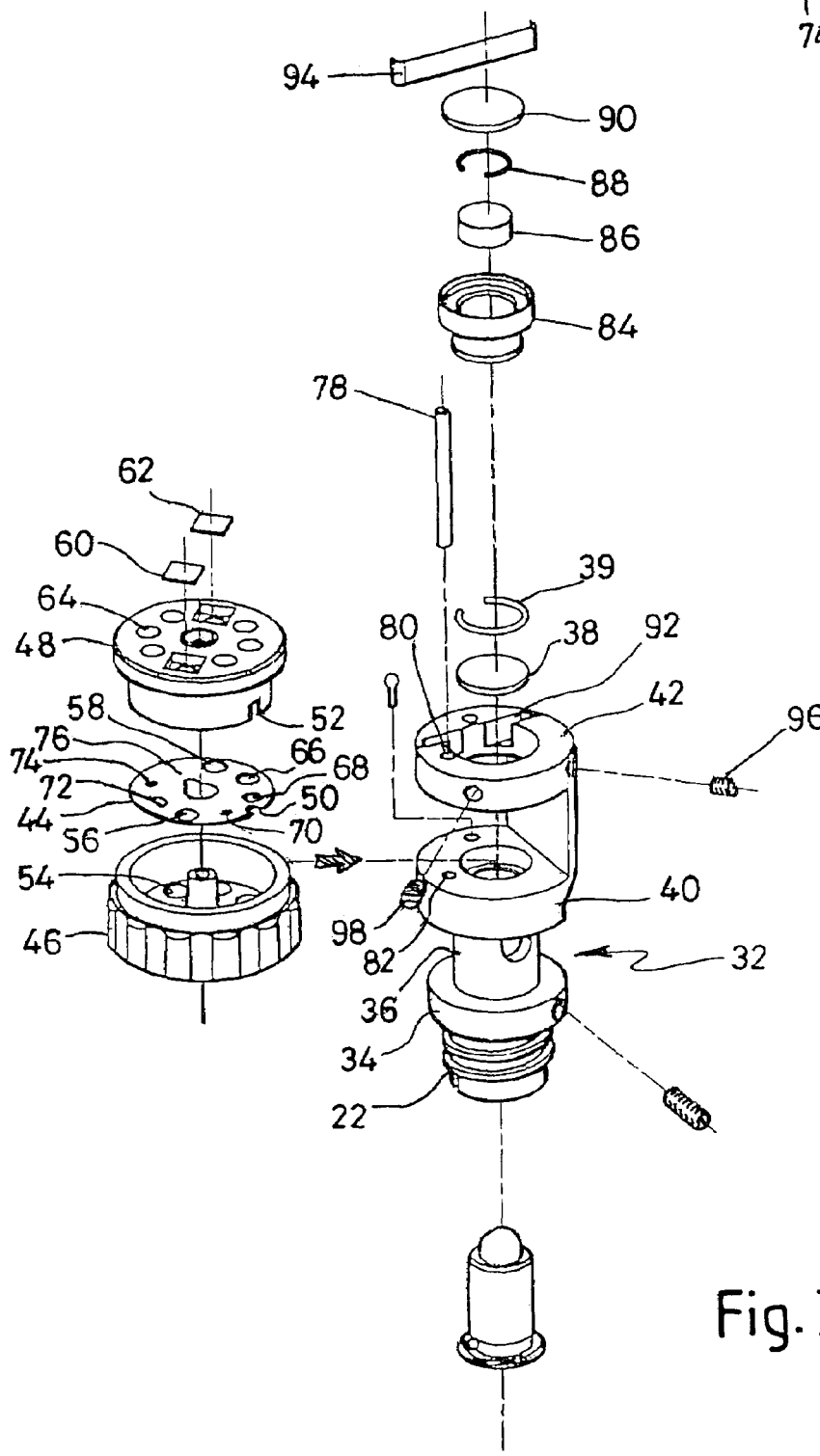
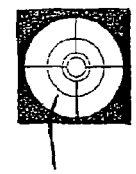
Fig. 3B
Fig. 3

OPHTHAMOSCOPE

FIELD OF THE INVENTION

This invention relates to ophthalmoscopes.

BACKGROUND TO THE INVENTION

Ophthalmoscopes are instruments used to view the fundus of an eye, and generally comprise a light source and a series of optical elements for directing illuminating light from the source into an eye under examination and imaging optics through which the illuminated fundus is viewed. In an indirect ophthalmoscope, a practitioner (or other user) views a real image of the fundus rather than the fundus itself.

A significant amount of the illuminating light beam is reflected from the cornea of an eye under examination, and it is important that these reflections are not seen by the practitioner/user as they will obscure the view of the fundus under examination. U.S. Pat. No. 3,586,424 shows an ophthalmoscope in which corneal reflexes are blocked by a single stop between an objective and an eye piece lens system of the ophthalmoscope. WO 00/30527 shows an ophthalmoscope in which illuminating light is reflected by a reflector within the ophthalmoscope itself towards the ophthalmoscope's objective lens systems. The lens system focuses the illuminating light to an apex at the cornea of an eye under examination. The reflector and the apex are substantially conjugate with each other so that the reflector acts as a stop for the corneal reflex.

However, despite these stops, both types of ophthalmoscope allow some corneal glare to obscure the viewed image.

SUMMARY OF THE INVENTION

According to the invention, there is provided an ophthalmoscope comprising illuminating optics for projecting a beam of light into an eye under examination and a housing containing imaging optics for creating an image of said eye for viewing by a user, the imaging optics comprising an objective lens system and an eye piece lens system, wherein the ophthalmoscope includes two corneal reflex stops situated one on either side of the corneal image formed by the objective lens system in use, to block reflections from the cornea of the eye under examination.

Preferably, the ophthalmoscope is an indirect ophthalmoscope.

Preferably, the housing also contains the illumination optics.

The two spaced apart corneal reflex stops are particularly effective at blocking the corneal reflex because the two spaced apart stops to block the corneal reflex from patients at varying distances from the ophthalmoscope. This flexibility is not provided by prior art ophthalmoscopes, in which it is attempted to provide a single corneal reflex stop at the image of the cornea, since the effectiveness of the stop is then highly sensitive to the distance of the patient from the instrument.

Preferably, each corneal reflex stop has a straight edge, preferably horizontal in use, the portion of the stop adjacent to said edge blocking the reflex. Preferably, the stops each have a part circular aperture, the edge forming a chord of said aperture.

Preferably, the ophthalmoscope includes an inverting lens interposed between the objective and eye piece lens systems, the inverting lens being operable to cause an erect, non-laterally inverted image of an eye under examination to be viewed through the eye piece.

The reflex stops are preferably positioned one on either side of the inverting lens.

Preferably, the two corneal reflex stops are separated by at least 10 mm. Preferably, the straight edge of each corneal reflex stop is spaced 2 mm from the optical axis of the ophthalmoscope.

Preferably, the ophthalmoscope includes a field stop at the position at which the objective lens systems forms an image of the retina of an eye under examination.

Such a field stop can be used to reduce glare from light reflected from the optical surfaces of the ophthalmoscope, and to reduce the glare from light scattered from the non optical surfaces.

The ophthalmoscope may to advantage also include a further field stop, preferably at the position at which the inverting lens forms an image of the retina of an eye under examination.

Such a field stop can be used to define the field of view of the ophthalmoscope and can further reduce glare from light scattered from the non-optical surfaces.

The field stops may to advantage be positioned one on either side of the corneal reflex stops so that the latter are situated between the field stops.

Preferably, the ophthalmoscope includes a front stop, situated in front of the first said field stop and operable to block lenticular reflexes from the eye under examination. In particular, the front stop is preferably operable to block the fourth Purkinje reflex, i.e. the reflex from the rear of the lens of the eye under examination.

Although the fourth Purkinje reflex is of a very low intensity relative to the corneal reflex, it is bright in relation to the image of the illuminated retina. Certain designs of ophthalmoscope use polarising filters to remove the corneal and lenticular reflexes, but in so doing also filter out potentially useful features from the image of the illuminated retina. The front stop therefore enables the illuminated retina to be viewed without interference of the fourth Purkinje reflex and without the loss of information which would be caused by polarisers.

Preferably, the illuminating optics are adjustable so as to enable the alignment of the illuminating light with the field viewed through the imaging optics and/or to enable the blocking of the corneal reflex by said reflex stops.

Preferably, the illuminating optics comprise a light source vertically spaced from the imaging optics, and a reflector for reflecting light from the source towards an eye under examination, the reflector being movable, preferably by being pivotable about two non-parallel axes to achieve said adjustability.

In this latter case, the reflector is preferably pivotable about a vertical axis and a horizontal axis perpendicular to the viewing direction from the ophthalmoscope to an eye under examination.

Preferably, the reflector is a partial reflector, such as a half silvered mirror.

The adjustability of the reflector provides an opportunity (for example for the manufacturer) to ensure that the ophthalmoscope is properly set up to illuminate a retina under examination whilst blocking unwanted reflexes.

The illuminating optics may to advantage include a focussing lens which is movable relative to a light source in a direction lateral to the path of the illuminating light though the illuminating optics. This enables the position of a projected image on the retina of an eye under examination to be adjusted.

Preferably, the ophthalmoscope illuminating optics include a graticule for projecting an image onto the eye under examination.

Preferably, the graticule is mounted on a support on which there is also provided at least one stop, the support being movable to bring either the stop or the graticule into registry with the path of the illuminating light through the illuminating optics, to enable image of the stop or the graticule either to be projected onto the eye under examination.

Preferably, the support comprises a rotatable plate.

The reflector may to advantage be situated in front of the objective lens system. As a result the beam of illuminating light does not pass through any of the optical elements of the imaging optics before it reaches the eye under examination, thus reducing or avoiding reflections from those elements.

The ophthalmoscope may include focusing means comprising a control and a linkage connecting the control to a lens means in the viewing system, the linkage comprising a bent flexible rod so arranged that the lens is moved along the viewing path by non parallel movement of the control.

This provides a very simple, and inexpensive, mechanism linking the control on, for example, a handle of the ophthalmoscope to a lens of the imaging optics.

Preferably said control is slideable.

Preferably said sliding movement of the control is in a direction perpendicular to the viewing direction from the objective lens system to an eye under examination.

For example, the control may be a slider mounted on a handle projecting vertically down from the ophthalmoscope body.

Preferably, the lens means which is connected to the linkage is the eye piece lens system.

The ophthalmoscope may to advantage provide adjustable magnification of the image of an eye under examination, and to that end preferably includes two interchangeable inverting lens systems of differing magnifying powers which are moveable so that either system may be moved into registry with the objective and eye piece lens system.

Alternatively the adjustable magnification can be achieved by providing a single inverting lens systems which is moveable along the optical axis of the imaging optics.

Thus the user can select the magnification and field of view appropriate for inspecting the features of interest in a retina under examination, the high magnification being more appropriate for obtaining a more detailed view of any given localised features, whilst the lower magnification is potentially advantageous when as much of the retina as possible needs to be examined in one view.

Preferably, the two interchangeable inverting lens systems are mounted on a common cradle pivotally mounted in the ophthalmoscope so as to be moveable from one angular position, in which one of the inverting lens systems is in registry with the objective and eye piece lens systems, into another angular position in which the other inverting lens system is in registry with the eye piece and objective lens systems, only a respective one of the inverting lens systems being in registry with the objective and eye piece systems for each of the angular positions of the cradle.

Preferably, the cradle is retained in each of said positions by a respective magnetic fastener.

The ophthalmoscope may to advantage include a rest extending from the rear of the eye piece, the rest being operable to control the proximity of the user's eye to the eye piece lens assembly, and being extendible so that the ophthalmoscope has the same or similar viewing characteristics for a user with or without spectacles.

If the practitioner's/user's eye is located significantly away from said optimum proximity to the eyepiece lens either forwards or backwards along the optical axis then only part of the field of view of the ophthalmoscope will be visible. In the extended position the rest is operable to locate the eye of a user who is not wearing spectacles. In the retracted position the rest is operable to locate the eye of a user who is wearing spectacles.

The imaging optics can therefore provide a full field of view for spectacle wearing and non-spectacle wearing users.

BRIEF DESCRIPTION OF THE DRAWINGS

The invention will now be described, by way of example only, with reference to the accompanying drawings in which:

FIG. 3 is an exploded perspective view of the lower portion of the illuminating optics of the ophthalmoscope;

DETAILED DESCRIPTION

Figure 1:
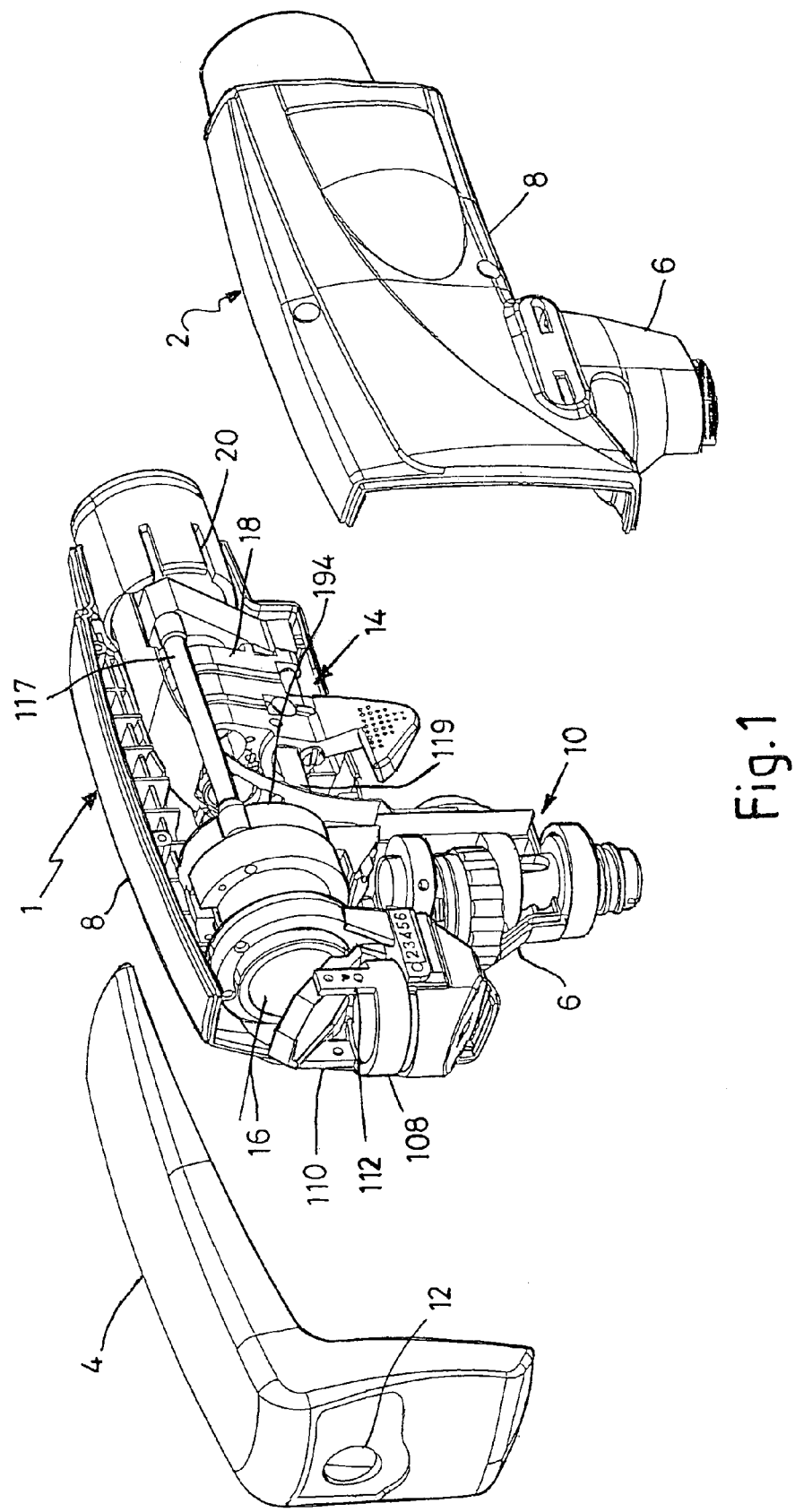
FIG. 1 is partially exploded perspective view of an indirect ophthalmoscope in accordance with the invention.

With reference to FIG. 1, an ophthalmoscope in accordance with the invention comprises a housing having two side sections 1 and 2 which are mirror images of each other and a front and top housing section 4 which extends over the tops of the housing sections 1 and 2 and down the front of the ophthalmoscope. Each side section has a handle portion 6 extending from a main body portion 8. The handle portions 6 extend vertically from the main portion 8, and contains illuminating optics 10 for projecting a beam of illuminating light through a window 12 in the front of the housing section 4. The portion of the housing section 4 defining the window 12 constitutes a front stop of the ophthalmoscope. The volume defined by the body portions of the housing sections 1 and 2 contains the ophthalmoscope's imaging optics, generally referenced 14.

The imaging optics 14 include an objective lens system 16 from which light from an eye under examination passes through either one or two intermediate inverting lens systems in a common cradle 18 to an eye piece lens system 20 through which a real erect, non-inverted image of the retina under examination can be viewed.

The imaging and illuminating optics will now be described.

Figure 2:
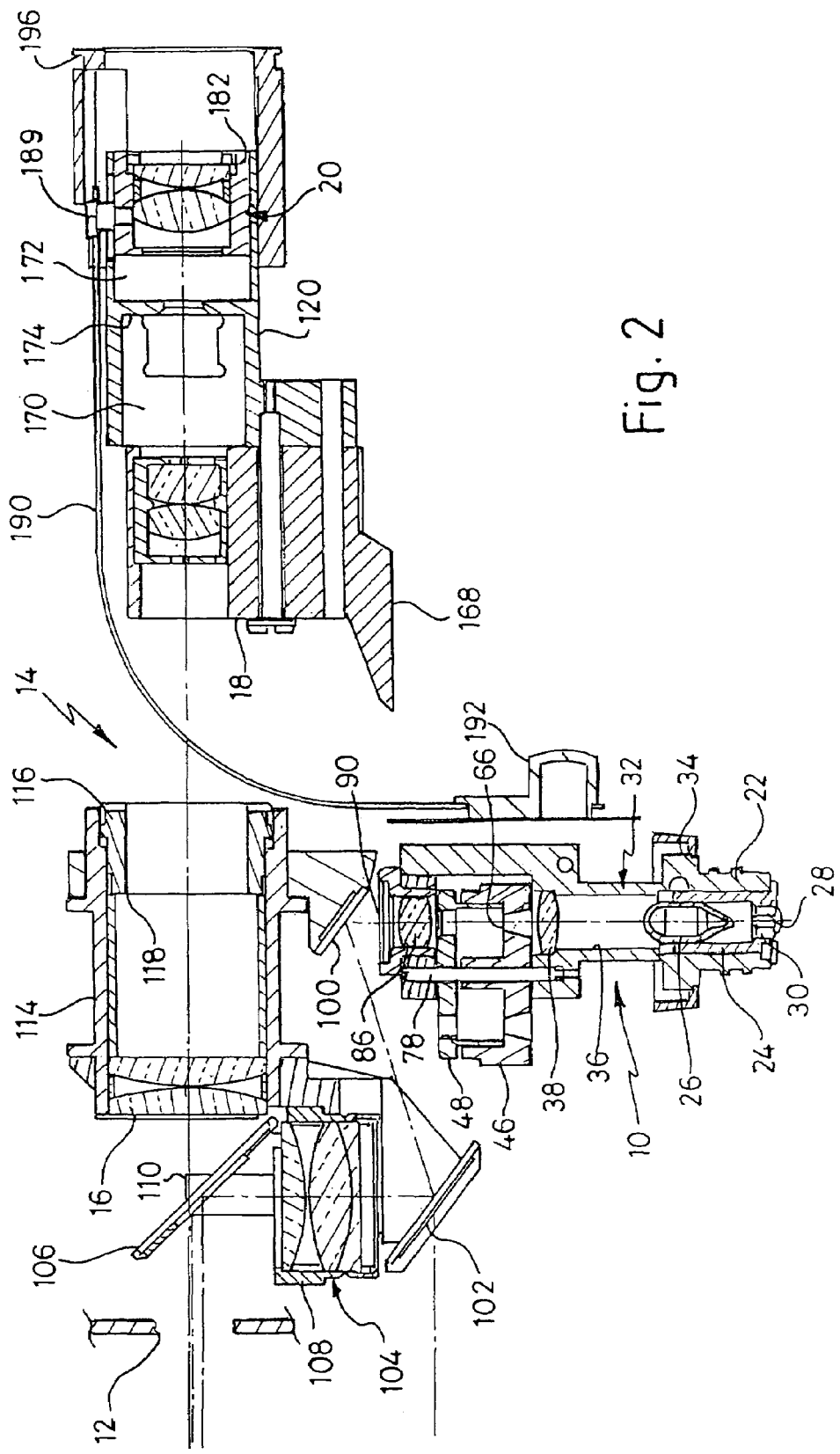
FIG. 2 is a sectional side view of the ophthalmoscope with its outer casing removed.

With reference to FIGS. 1 and 2, the illuminating optics 10 include a lower screw threaded connector 22 which surrounds a lamp holder 24 in which a halogen light bulb 26 is held in electrical contact with lower terminals 28 and 30. In use, the screw threaded connector 22 releasably connects the bulb to a battery pack (not shown) which is incorporated into a handle, supplies power for operating the bulb 26 and which includes on-off and brightness controls.

With reference to FIG. 3, the connector 22 forms an integral part of an annular support 32 having a lower flange 34 for acting as a mechanical stop against which the battery pack abuts, and a concentric connecting tube 36 at the top of which there is provided a focusing lens 38 at a position coaxial with the filament of the bulb 26. The lens 38 retained by means of a spring clip 39 located in a lower flange 40 of the member 32, which also has a top flange 42 spaced from the flange 40 to define a space for accommodating a stop and graticule plate 44 sandwiched between a knurled wheel 46 and a upper filter holder 48.

The wheel 46 forms the outer periphery of a cylindrical member which includes an axial spigot (not shown) in registry with slots 50 and 52 in the graticule/stop plate 44 and the filter holder 48 respectively. The spigot matingly engages the slots 50 and 52 so that the plate 44 and holder 48 are angularly located relative to the wheel 46 so as to rotate with the latter.

The underside of the member constituting the wheel 46 is provided with a series of apertures, for example 54, each in registry with a respective formation on the plate 44. Two of those formations are simple apertures 56 and 58, each in registry with the respective one of a cobalt blue filter 60 and a red-free, green filter 62 in the filter holder. The filter holder also includes circular apertures, for example, 64, each in registry with a respective one of the formations in the plate 44.

Turning to the remaining formations on the plate 44, the aperture 66 is a wide angle aperture for illuminating the largest area of the fundus of the eye under examination for the best possible diagnosis through dilated pupils. The aperture 68 is an intermediate aperture which permits easier viewing through an undilated pupil in peripheral examination. This aperture provides illumination which is particularly useful in paediatric examination. The aperture 70 is of a smaller diameter still and is intended for use in illuminating the retina for viewing of the macular area of the fundus or through a small pupil. The use of this aperture reduces pupillary reaction and improves patient comfort. Aperture 72 is a half-moon aperture which provides a combination of depth perception and good field of view whilst aperture 74 contains a graticule (shown in detail in FIG. 3A) which is projected onto the retina to assess the cup/disc ratio as an aid to glaucoma diagnosis and monitoring.

The assembly of the wheel 46, plate 44 and holder 48 is provided with a through passage through which a spindle pin 78 extends. The pin also extends through apertures 80 and 82 in the member 40 and 42 to define an axis, eccentric with that of the tube 36, about which the assembly rotates. It will be appreciated that a user can select which of the formations on the plate 44 and/or which the filters 60 and 62 is to be in registry with the path of light from the bulb 26, and thereby selects a mode of operation of the ophthalmoscope from a number of possible alternatives.

The upper flange 42 of the holder has a central aperture which accommodates a relay lens holder 84 for a relay lens 86 held in position in the holder 84 by means of by a spring clip 88. At the top of the holder 84 there is provided an infrared filter 90. The top of the flange 42 is also formed with a slot 92 running along a chord of the flange 42, and accommodating a leaf spring 94 which acts against the holder 84 to urge it against one side of the circular portion of the aperture in the flange 42.

That aperture is of a larger diameter than that of the holder 84 so that the holder 84 may move along either of two horizontal perpendicular axes relative to the flange 42. The flange 42 includes a pair of radial screw threaded through bores, each of which accommodates a respective one of two grub screws 96 and 98. These screws act against the periphery of the lens holder 84, against the action of the spring 94, and enable the position of the lens 86 to be laterally adjusted, to achieve alignment of the illuminating light with the field viewed through the imaging optics 14.

A mirror 100 is positioned above the filter 90 and reflects light from the bulb 26 forwards and downwards onto a further angled mirror 102, which, in turn, reflects the light up through a projection lens system 104 onto an angled partially reflecting mirror 106. The mirror 106 is mounted on a turntable 108 which may rotate about a vertical axis passing through the centre of the mirror 106. The mirror is mounted on the turntable 108 by means of two vertical posts 110 and 112 on which the mirror is pivotably mounted so as to pivot about a horizontal axis which passes through the centre of the mirrors reflective surface and is in the plane of the latter. A light trap in the form of a matt black surface on the underside of the ophthalmoscope housing is situated immediately above the mirror 106 so as to trap any stray light passing there through from the mirror 102. The light that is reflected forwards to the mirror 106 passes through the window 12 and into the eye under examination.

Figure 4:
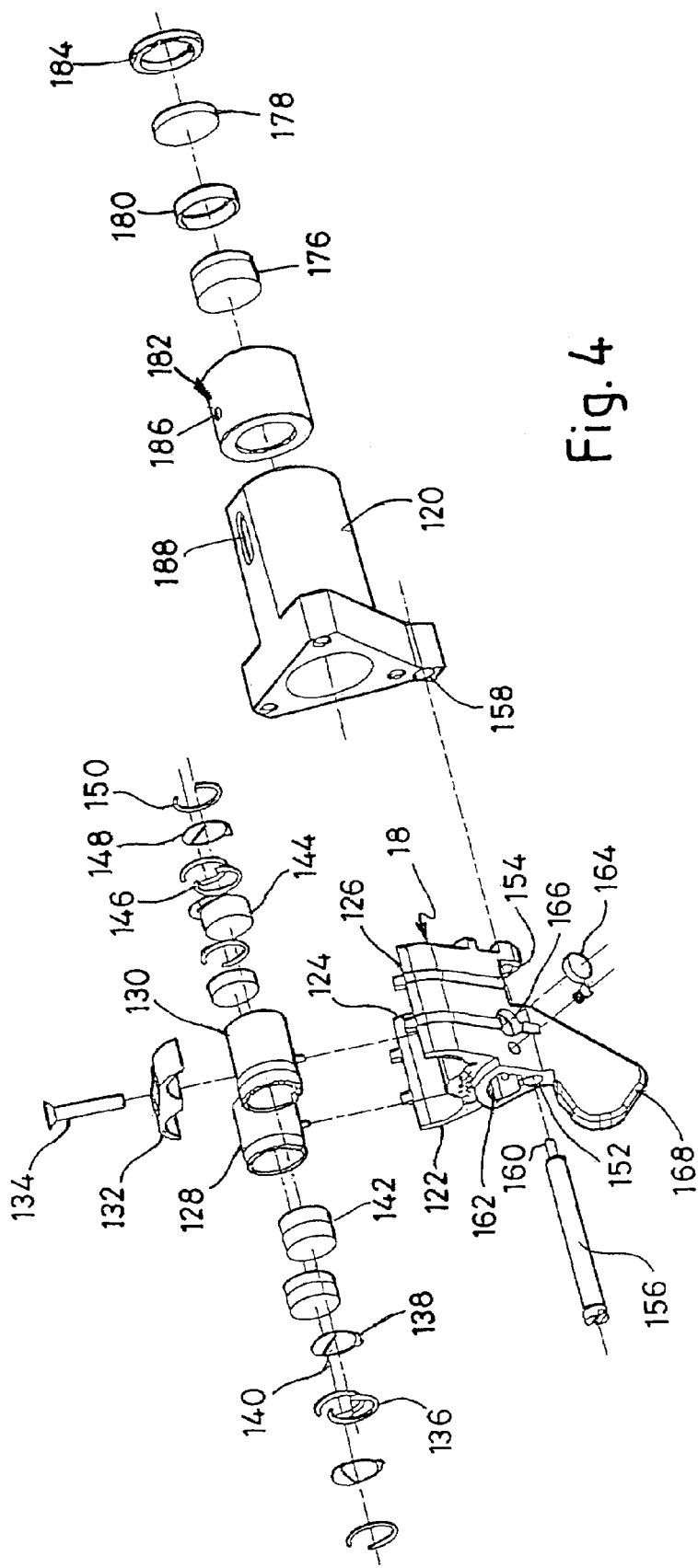
FIG. 4 is an exploded perspective view of part of the imaging optics of the ophthalmoscope.

In use, the mirror 106 is so orientated relative to the rest of the ophthalmoscope that the corneal reflex is blocked by the corneal reflex stops 138 and 148 shown in FIG. 4. The fourth Purkinje reflex is blocked by the front stop. Light from the eye under examination passes back through the window 12 and through the half silvered mirror 106 into the objective lens system 16. The lens system 16 is mounted in a cylindrical holder 114 and comprises two lenses. The holder 114 also contains a cylindrical insert 116 which is of a smaller internal diameter than that of holder 114 which positions a 12.4 mm diameter field stop 118 at 24.30 mm from the inner lens of the objective lens system 16. The underside of the holder 114 also carries mirror 100 and its holder.

The end of the holder 114 remote from the lens system 16 includes three sockets which are equiangularly spaced around the holder 14 and each of which accommodates an end of a respective rigid rod which extends to an eye piece holder 120 (which has corresponding sockets for the other ends of the rods) to fix the two holders relative to each other. In between the two holders 114 and 120 there is provided the cradle 18 shown in more detail in FIG. 4.

The cradle 18 has a lower portion 122 which defines two upwardly facing part cylindrical channels 124 and 126, each of which accommodates a respective one of two cylindrical holders 128 and 130 held in position by a cap 132 which is screwed (by screw 134) onto the portion 122 of the cradle.

Two of the rods are shown at 117 and 119 in FIG. 1.

The holder 130 has a machined step against which lens 144 and 142 abut. Wire clip 146 keeps lens 144 abutted with the machined step.

A corneal reflex stop 148 in the form of a ring shaped member having a generally D-shaped aperture, the top of which defines the lower straight edge of the stop, is located with a tab that extends vertically downwards from the outer edge and engages a corresponding slot in the holder 130 and abuts clip 146. Wire clip 150 abuts stop 148. Stop 138 abuts lens 142 and its tab locates in similar fashion to stop 148. Wire clip 136 abuts stop 138. Tabs on stop 138/stop 148 align with location pin in body of 130 to ensure correct alignment of stops in imaging optics. Locations pins in bodies 130 and 128 locate in slots in lower portion of part cylindrical channel 124 and 126.

The contents of the holder 128 are identical to those of the holder 130, save for the lenses which have a different power so that the inverting lens system in the holder 128 has different magnification from that provided by the lenses in the holder 130.

The forward portion of the cradle 18 includes a through bore 152 in registry with an aperture 154 in a rear lug on the underside of the cradle 18. A pivot 156 extends through the bore 152 and the aperture 154 so that the cradle 18 can pivot about the pin 156. The rearward end of the pin 156 includes a screw threaded connector 160 Which extends into a corresponding aperture 158 in the eye piece holder 120.

The cradle includes through a passage 162 immediately above the bore 152 and a lug defining an aperture 154 for accommodating the rod 119 which passes through the lower portion of the cradle with enough clearance to enable the cradle to assume either of two operating angular positions. The cradle also has a magnet 164 fixed in a recess 166 in one side of the cradle. A similar magnet and recess are provided on the opposite side. The magnets co-operate with ferromagnetic rod 119 to hold the cradle in either of its two angular positions. A control 168 extends from the bottom of the cradle 18 from the other side of the pivot axis defined by the pin 156 so that manipulation of the control 168 rocks the cradle 18 into either of its two angular operating positions.

In one of those operating positions, the holder 130 is in registry with the viewing path of the imaging optics, the holder 128 being clear of the viewing path, whilst in the other position the situation is reversed, i.e. the holder 130 is clear of the viewing path whilst the holder 128 is registry with the end path.

The eye piece holder 120 has a forward cylindrical passage 170 (FIG. 2) separated from a rear passage 172 by an annular shoulder 174.

The shoulder 174 constitutes the eye piece field stop which is of a diameter of 5.3 mm, and which helps to cut down glare from reflections from the optical surfaces of the ophthalmoscope and reduces glare due to light scattered from the non-optical surfaces. The stop in shoulder 174 is at the infinity focus of the objective and inverting lens systems.

The eye piece lens systems comprises an achromatic doublet 176 and a further lens 178 separated from each other by a spacer ring 180 and held in position in a cylindrical eye piece lens holder 182 by a spring clip 184.

In the top of the holder 182 there is provided a screw threaded bore 186 which is in registry with a top slot 188 in the eye piece holder 120.

A screw 189 extends through the slot 188 and into the bore 186 so as to attach a flexible strip 190 to the eye piece lens holder 182.

The strip 190 curves through 90° and is terminated at a control slider 192. The strip includes a central elongate aperture 194 (FIG. 1) so that it does not obscure the viewing path.

The strip is flexible so that vertical movement of the slider 192 is transmitted by the strip to the eye piece lens holder 182 to cause horizontal movement of the latter. The strip 190 thus acts as a flexible connecting rod between the control slider 192 and the eye piece lens system, so as to provide a focusing control for the ophthalmoscope. The ophthalmoscope also includes a slideable rear cylindrical casing portion 196 which is slideably mounted in the ophthalmoscope housing and is movable from an extended position, as shown in FIG. 2, to a retracted position in which the outboard end of the portion 196 is adjacent to the eye piece lens system. If the user is wearing spectacles, the portion is to be placed in its retracted condition, whereas the extended position would be used by a user who is not wearing spectacles. Thus the distance of the eye of the user from the eye piece lens system remains the same, whether or not the user is wearing spectacles.

In use, the user selects a suitable brightness level for the halogen bulb 26 (using controls on the battery casing). The user also selects the appropriate inverting lens system using the control 168.

The lens system contained in the holder 128 causes the ophthalmoscope to have a field of view of 17.5° and magnification of 1.5 (corresponding to a retinal magnification of 22.5), whilst the inverting lens system contained in the holder 130 causes the ophthalmoscope to have a 25° field of view and a magnification of 1.0 (retinal magnification of 15).

Figure 7:
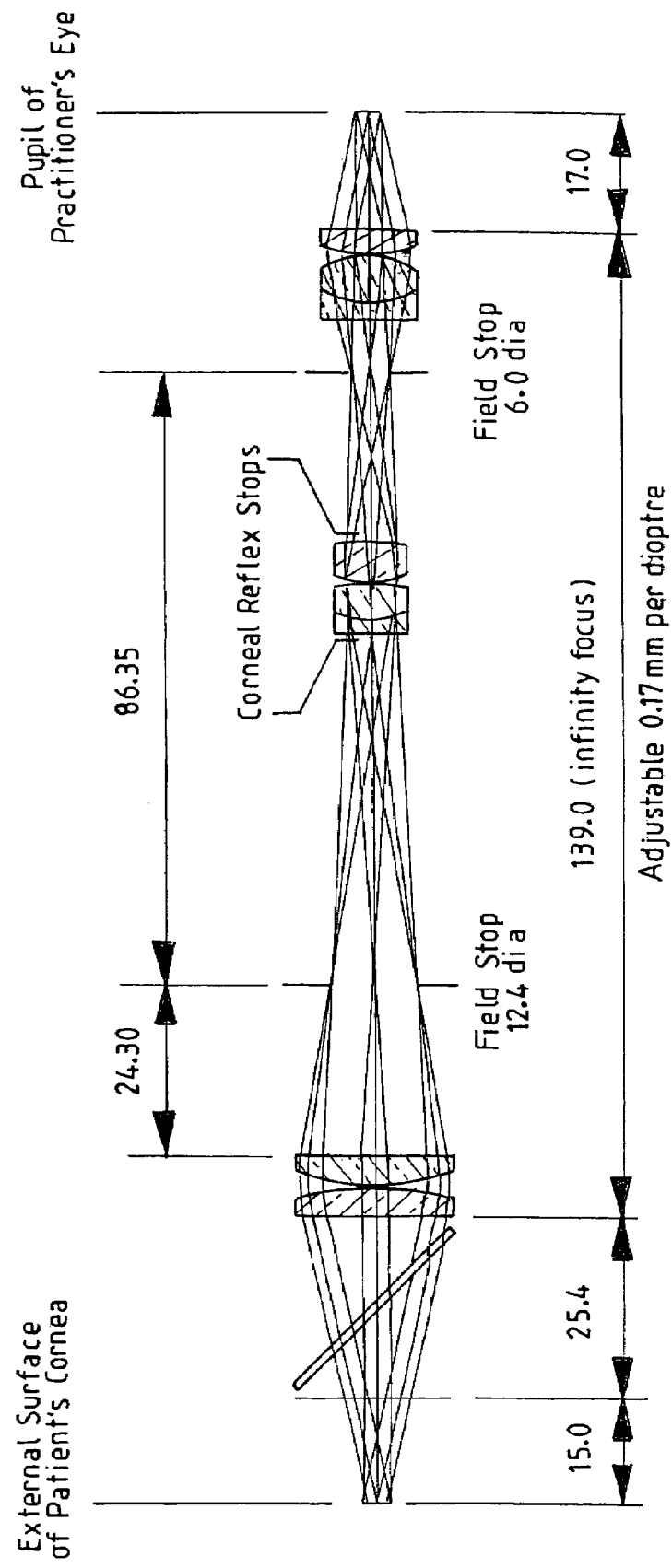
FIG. 7 is a ray diagram showing the imaging optics in operation.

The distance between corneal stops in the holder 128 is 11.5 mm (plus or minus 1 mm) whilst that of the stops in the holder 130 is 13.9 mm (plus or minus 1 mm). Various other distances between the optical elements in the imaging optics are shown in FIG. 7.

Figure 5:
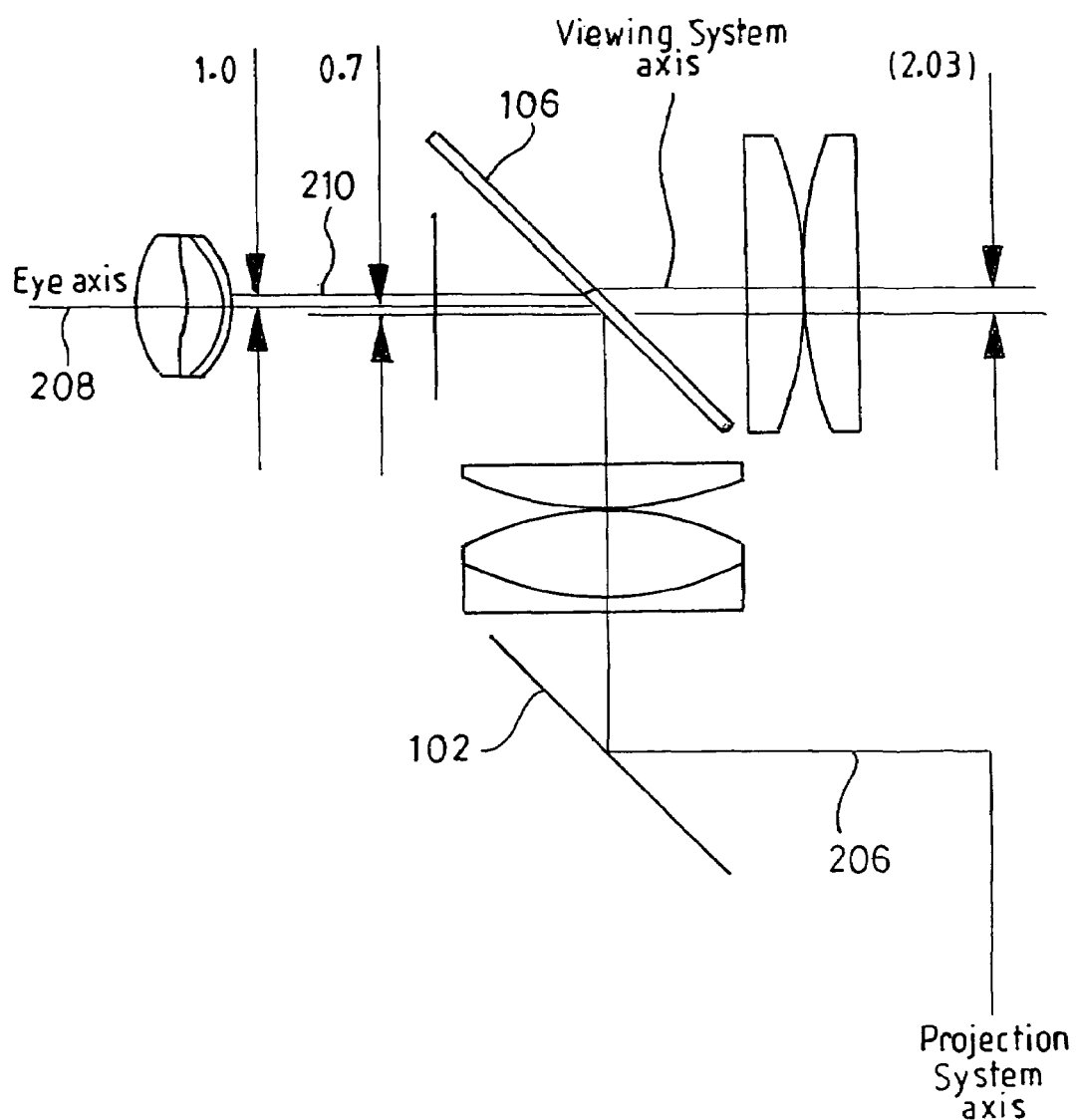
FIG. 5 is a diagram showing the relative positions of the illumination and viewing paths for the ophthalmoscope.
Figure 6:
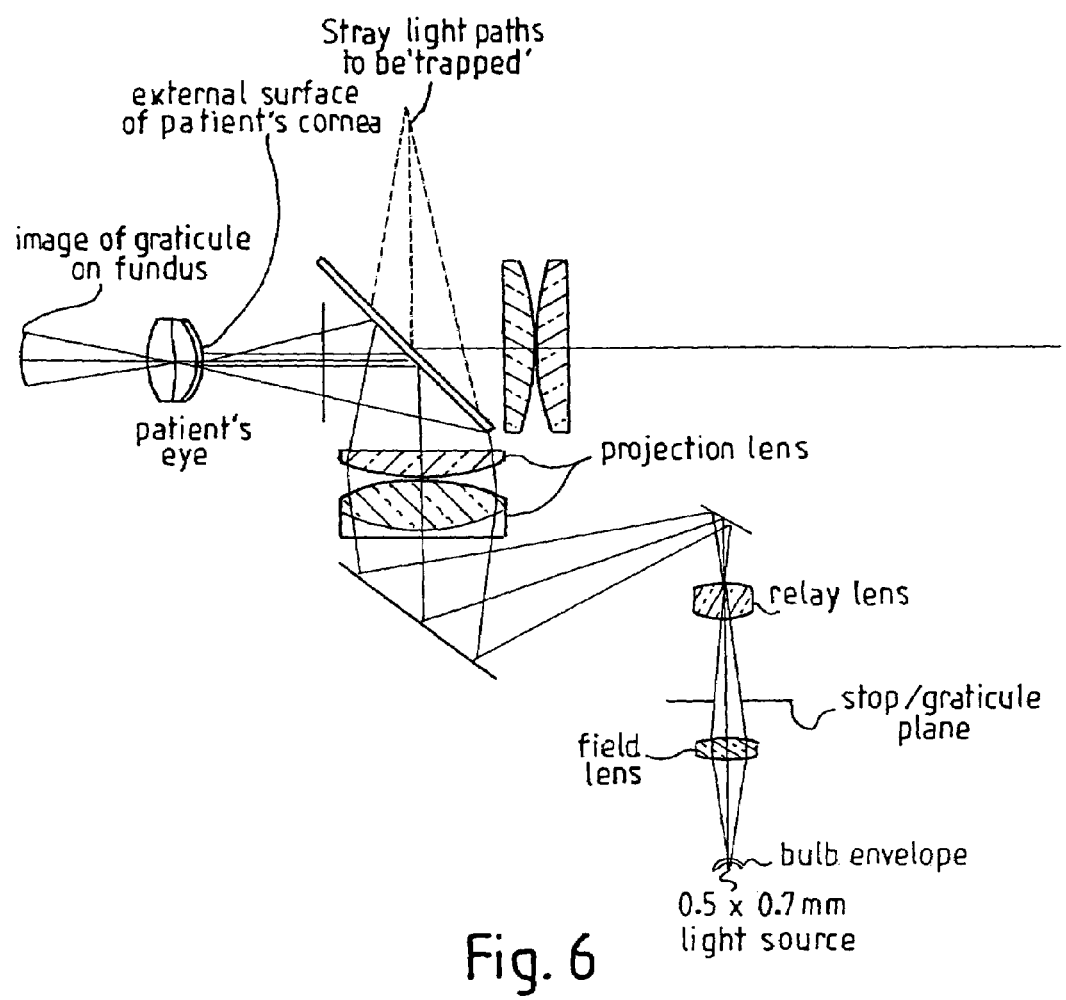
FIG. 6 is a ray diagram showing the illuminating optics in action.

As can be seen from FIG. 5, the illuminating beam axis 206 extends, in use vertically upwards from the mirror 102 to intersect the mirror 106 at a position 0.7 mm vertically beneath the point at which the axis (208) of the eye under examination intersects the mirror 106. The optical axis 218 of the viewing system intersects the front of the mirror 106 at a position 1 mm vertically above the point of intersection of the eye axis, so that the illumination and viewing axis are spaced from each other by 1.7 mm. The refraction caused by the mirror 106 on the light passing through it to the imaging optics increased the vertical distance between the viewing and illumination axes to 2.03 mm.

The operation of the ophthalmoscope will now be described.

Initially the user looks at the patients eye through the ophthalmoscope from some distance away from the patient's eye so that the user can see the patient's pupil and centre it in the field of view. Then by adjusting the angle of the ophthalmoscope the user can view a small part of the retina through the pupil. This partial view is seen as a red patch. The user then moves towards the patient maintaining the view of the retina. As the user gets closer to the patient more and more of the retina can be seen. At some point the corneal reflex becomes obvious and, if not blocked, will be so bright that the retinal image can be longer be seen. At this point the angle of the ophthalmoscope is adjusted to 'move' the reflex behind the front reflex stop. This is the condition shown in FIG. 8(a) where the front reflex stop 138 completely blocks the corneal reflex. At this point a large area of the retina can be seen but the user has to move even closer to acquire the full available view. As the user moves closer the front reflex stop is less effective. The rear reflex stop 148 now blocks that part of the reflex which is not blocked by the front reflex stop. The two stops working together enable the reflex to be completely blocked down to, and beyond, the point at which the full field-of-view can be seen as shown in FIG. 8(b).

Figure 8A:
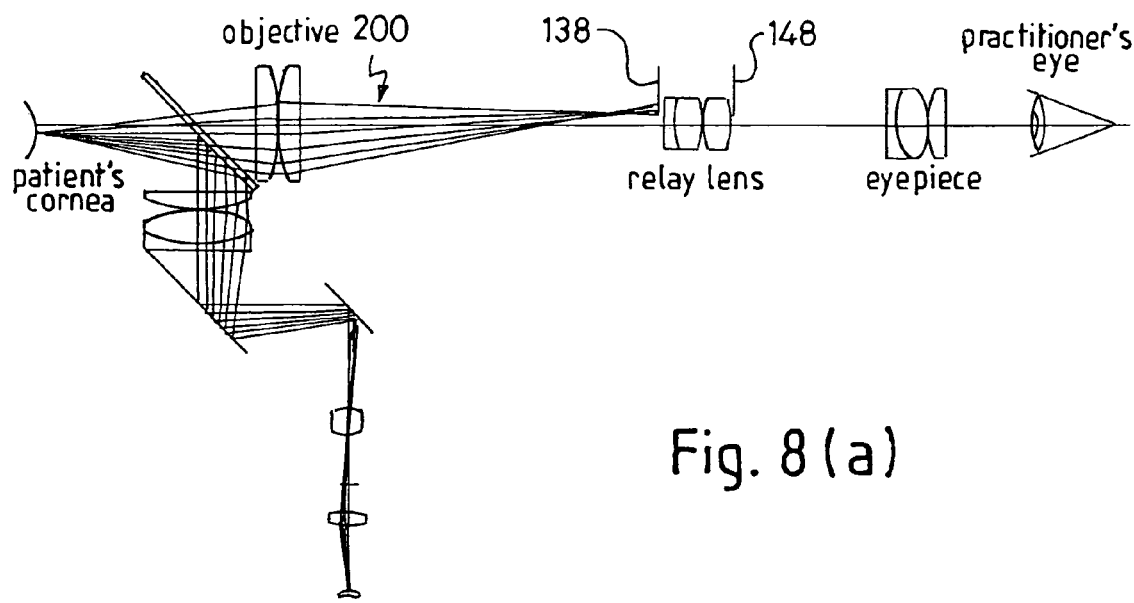
FIGS. 8(*a*) and (*b*) are ray diagrams showing how the corneal reflex from an eye under examination is blocked.

FIG. 8(a) shows the fan of rays 200 which, but for the stop 138, could reflect off the cornea and be transmitted through to the practitioner's eye giving a strong corneal reflex (much stronger than the retinal image). These rays are, however, completely blocked by the front reflex stop 138. Note that only rays through the rear half of the relay lens can contribute to a corneal reflex; rays through the front half of the lens are reflected outside the field of view by the cornea.

Figure 8B:
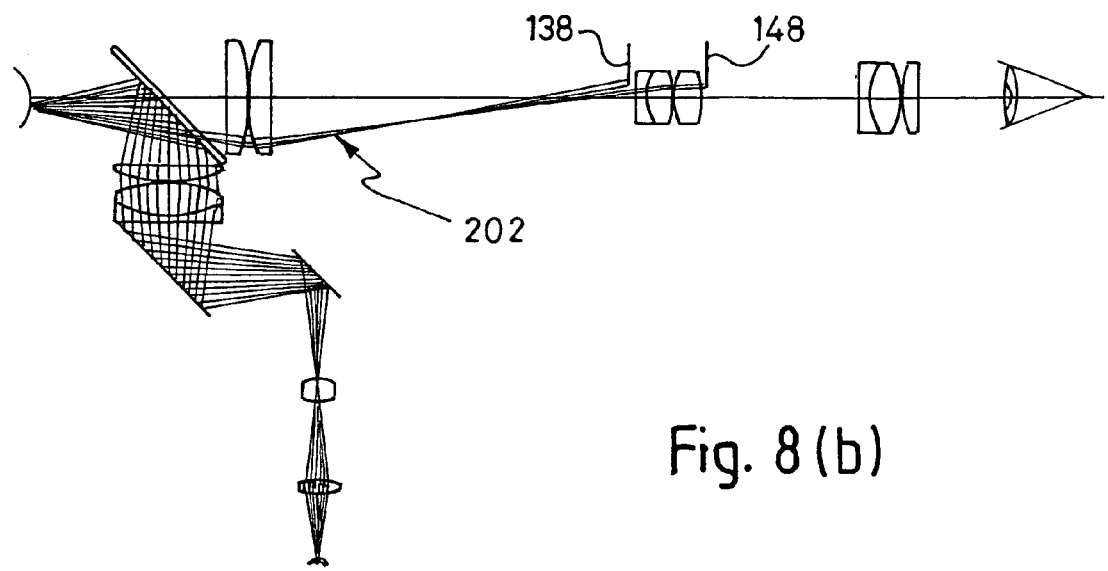

FIG. 8(b) shows that a complete fan of rays 202 could contribute to a reflex, if the ophthalmoscope is moved closer to the patients eye. In this situation however, the rays are completely blocked by one or other of the two reflex stops 138, 148.

The reflex stops are especially effective because i) they are positioned close to the image of the cornea produced by the objective lens system 16.

and/or ii) the illumination system is designed to project a small image of the filament near to the cornea.

Ideally the filament would be imaged at the cornea but this is not consistent with projecting the maximum amount of light onto the retina. This latter condition is achieved by imaging the filament onto the patient's pupil—some 3 mm distant behind the cornea. The compromise is to project the filament image to be between the pupil and the cornea.

The image of the cornea is in the centre of the inverting lens system 142, 144 and it would be difficult to place a stop here. The compromise has been to put stops on either side of these lenses. This has had the considerable advantage of increasing the range of distance between the ophthalmoscope and patient over which the corneal reflex can be effectively blocked.

The invention claimed is:

1. An ophthalmoscope comprising illuminating optics for projecting a beam of light into an eye under examination and a housing containing imaging optics for creating an image of said eye for viewing by a user, the imaging optics comprising an objective lens system and an eye piece lens system, wherein the ophthalmoscope includes two corneal reflex stops situated one on either side of the corneal image formed by the objective lens system in use, to block reflections from the cornea of the eye under examination.

2. An ophthalmoscope according to claim 1, in which the ophthalmoscope is an indirect ophthalmoscope.

3. An ophthalmoscope according to claim 1 in which the housing also contains the illuminating optics.

4. An ophthalmoscope according to claim 1, in which each corneal reflex stop has a straight edge, the portion of the stop adjacent to said edge blocking the reflex.

5. An ophthalmoscope according to claim 4, in which each said straight edge is horizontal in use.

6. An ophthalmoscope according to claim 4, in which the stops each have a part circular aperture, the edge forming a chord of said aperture.

7. An ophthalmoscope according to claim 4, in which the straight edge of each corneal reflex stop is spaced 2 mm from the optical axis of the ophthalmoscope.

8. An ophthalmoscope according to claim 1, in which the ophthalmoscope includes an inverting lens interposed between the objective and eye piece lens systems, the inverting lens being operable to cause an erect, non-laterally inverted image of an eye under examination to be viewed through the eye piece.

9. An ophthalmoscope according to claim 8, in which the reflex stops are positioned one on either side of the inverting lens.

10. An ophthalmoscope according to claim 8, in which the ophthalmoscope includes a field stop at the position at which the objective lens systems forms an image of the retina of an eye under examination.

11. An ophthalmoscope according to claim 10, in which the ophthalmoscope includes a further field stop.

12. An ophthalmoscope according to claim 11, in which said further field stop is at the position at which the inverting lens forms an image of the retina of an eye under examination.

13. An ophthalmoscope according to claim 10, in which the field stops are positioned one on either side of the corneal reflex stops so that the latter are situated between the field stops.

14. An ophthalmoscope according to claim 10, in which the ophthalmoscope includes a front stop, situated in front of the first said field stop operable to block lenticular reflexes from the eye under examination.

15. An ophthalmoscope according to claim 14, in which the front stop is operable to block the fourth Purkinje reflex.

16. An ophthalmoscope according to claim 1, in which the two corneal reflex stops are separated by at least 10 mm.

17. An ophthalmoscope according to claim 1, in which the illuminating optics are adjustable so as to enable the alignment of the illuminating light with the field viewed through the imaging optics and/or to enable the blocking of the corneal reflex by said reflex stops.

18. An ophthalmoscope according to claim 17, in which the illuminating optics comprise a light source vertically spaced from the imaging optics, and a reflector for reflecting light from the source towards an eye under examination, the reflector being movable to achieve said adjustability.

19. An ophthalmoscope according to claim 18, in which the reflector is pivotable about a vertical axis and a horizontal axis perpendicular to the viewing direction from the ophthalmoscope to an eye under examination.

20. An ophthalmoscope according to claim 19, in which reflector is a partial reflector.

21. An ophthalmoscope according to claim 17, in which the reflector is situated in front of the objective lens system.

22. An ophthalmoscope according to claim 17, in which the illuminating optics include a focussing lens which is movable relative to a light source in a direction lateral to the path of the illuminating light though the illuminating optics.

23. An ophthalmoscope according to claim 1, in which the illuminating optics include a graticule for projecting an image onto the eye under examination.

24. An ophthalmoscope according to claim 23, in which the graticule is mounted on a support on which there is also provided at least one stop, the support being movable to bring either the stop or the graticule into registry with the path of the illuminating light through the illuminating optics, to enable image of the stop or the graticule either to be projected onto the eye under examination.

25. An ophthalmoscope according to claim 24, in which the support comprises a rotatable plate.

26. An ophthalmoscope according to claim 1, in which the ophthalmoscope includes focusing means comprising a control and a linkage connecting the control to a lens means in the imaging optics, the linkage comprising a bent flexible rod so arranged that the lens means is moved along the viewing path by non parallel movement of the control.

27. An ophthalmoscope according to claim 26 in which said control is slideable.

28. An ophthalmoscope according to claim 27, in which said sliding movement of the control is in a direction perpendicular to the viewing direction from the objective lens system to an eye under examination.

29. An ophthalmoscope according to claim 26, in which the lens means which is connected to the linkage is the eye piece lens system.

30. An ophthalmoscope according to claim 1, in which the ophthalmoscope provides adjustable magnification of the image of an eye under examination.

31. An ophthalmoscope according to claim 30, in which said adjustable magnification is achieved by means of two interchangeable inverting lens systems of differing magnifying powers which are moveable so that either system may be moved into registry with the objective and eye piece lens system.

32. An ophthalmoscope according to claim 31, in which the two interchangeable inverting lens systems are mounted on a common cradle pivotally mounted in the ophthalmoscope so as to be moveable from one angular position, in which one of the inverting lens systems is in registry with the objective and eye piece lens systems, into another angular position in which the other inverting lens system is in registry with the eye piece and objective lens systems, only a respective one of the inverting lens systems being in registry with the objective and eye piece systems for each of the angular positions of the cradle.

33. An ophthalmoscope according to claim 32, in which the cradle is retained in each of said positions by one or more magnetic fasteners.

34. An ophthalmoscope according to claim 1, in which the ophthalmoscope includes a rest extending from the rear of the eye piece, the rest being operable to control the proximity of the user's eye to the eye piece lens assembly, and being extendible so that the ophthalmoscope has the same or similar viewing characteristics for a user with or without spectacles.

\* \* \* \* \*